United States Patent [19]

Wätjen et al.

[11] Patent Number: 5,242,918
[45] Date of Patent: Sep. 7, 1993

[54] ISATINOXIME DERIVATIVES, THEIR PREPARATION AND USE

[75] Inventors: Frank Wätjen, Herlev; Bjarne H. Dahl, Copenhagen; Jørgen Drejer, Vaerlose; Leif H. Jensen, Copenhagen, all of Denmark

[73] Assignee: NeuroSearch A/S, Glostrup, Denmark

[21] Appl. No.: 936,579

[22] Filed: Aug. 27, 1992

Related U.S. Application Data

[63] Continuation-in-part of Ser. No. 831,851, Feb. 5, 1992, abandoned, which is a continuation-in-part of Ser. No. 751,165, Aug. 28, 1991, abandoned.

[51] Int. Cl.⁵ .............. A61K 31/555; C07D 491/048
[52] U.S. Cl. ..................... 514/215; 540/521; 546/81; 548/430; 514/292; 514/411
[58] Field of Search ............. 540/521; 546/81; 548/430; 514/215, 292, 411

[56] References Cited

U.S. PATENT DOCUMENTS 3,472,872 10/1969 Bell .......................... 540/430

Primary Examiner—Robert T. Bond
Attorney, Agent, or Firm—Gordon W. Hueschen

[57] ABSTRACT

A compound having the formula

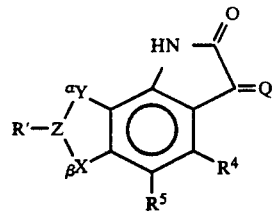

wherein
$R^4$ and $R^5$ independently are hydrogen, halogen, $CF_3$, $CN$, $NO_2$ or $SO_2NR^1R^2$ wherein
$R^1$ is hydrogen or straight, $C_{1-6}$-alkyl which may be branched or cyclic,
$R^2$ is hydrogen or straight, $C_{1-6}$-alkyl which may be branched or cyclic,
or wherein $R^1$ and $R^2$ together represent $-(CH_2)_n-A-(CH_2)_m-$, wherein A is O, S, $CH_2$ or $NR^I$, wherein $R^I$ is H, $C_{1-6}$-alkyl which may be straight, branched or cyclic, n is 0, 1, 2, 3, 4, 5 and m is 0, 1, 2, 3, 4, 5;
Q is NOH or O;
Z=O, S, N—$R^{II}$,

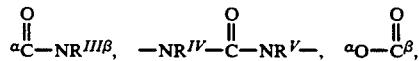

wherein $R^{II}$, $R^{III}$, $R^{IV}$ and $R^V$ independently are hydrogen, benzyl, $C_{1-6}$carboxylic acid-acyl, $C_{1-6}$-alkoxy which may be branched or cyclic, or $C_{1-6}$-alkyl which may be branched or cyclic;
X is $-(CH_2)_o-$ wherein o is 0, 1, 2, or 3;
Y is $-(CH_2)_p-$ wherein p is 0, 1, 2 or 3;
$\alpha$ and $\beta$ indicate attachment points,
and a method of treating disorders of a mammal, including a human, responsive to the blockade of glutamic and aspartic acid receptors, with the same.

10 Claims, No Drawings

ISATINOXIME DERIVATIVES, THEIR PREPARATION AND USE

The present application is a continuation-in-part of copending U.S. patent application Ser. No. 07/831,851 which was filed Feb. 5, 1992 now abandoned and which in turn is a continuation-in-part of U.S. patent application Ser. No. 07/751,165, filed Aug. 28, 1991, which has been abandoned.

The present invention relates to novel ring fused indole-2,3-dione oxime derivatives, a method of treatment therewith, pharmaceutical compositions comprising the compounds and to a method of preparing the novel compounds of the invention.

Object of the Invention

It is an object of the present invention to provide novel isatin derivatives which are useful in the treatment of diseases in mammals, including a human, and especially in the treatment of diseases which can be treated by antagonizing an excitatory amino acid of such mammal.

Another object of the present invention is to provide a method of treating diseases in mammals, including a human, responsive to the blockade of glutamic and aspartic acid receptors which comprises administering to a mammal in need thereof a compound of the invention.

A third object of the present invention is to provide novel pharmaceutical compositions for the treatment of diseases in mammals, including a human, responsive to the blockade of glutamic and aspartic acid receptors.

Background of the Invention

Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-aspartate (NMDA), the α-amino-3-hydroxy-5-methyl-4-isoxazole propionic acid (AMPA) receptor, and the kainate receptor. This excitotoxic action is responsible for the loss of neurons in cerebrovascular disorders such as cerebral ischemia or cerebral infarction resulting from a range of conditions, such as thromboembolic or haemorrhagic stroke, cerebral vasospasm, hypoglycaemia, cardiac arrest, status epilepticus, perinatal asphyxia, anoxia such as from drowning, pulmonary surgery and cerebral trauma as well as lathyrism, Alzheimer's, and Huntington's diseases.

The compounds of the present invention may also be useful in the treatment of schizophrenia, epilepsy, anxiety, pain and drug addiction.

EPA 432648, published Jun. 19, 1991, discloses certain isatineoxime derivatives.

SUMMARY OF THE INVENTION

The invention then, inter alia, comprises the following, alone or in combination:

A compound having the formula

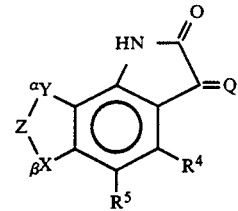

wherein
$R^4$ and $R^5$ independently are hydrogen, halogen, $CF_3$, CN, $NO_2$ or $SO_2NR^1R^2$ wherein
$R^1$ is hydrogen or $C_{1-6}$-alkyl which may be straight, branched or cyclic,
$R^2$ is hydrogen or $C_{1-6}$-alkyl which may be straight, branched or cyclic,
or wherein $R^1$ and $R^2$ together represent —$(CH_2)_n$—A—$(CH_2)_m$—,
wherein A is O, S, $CH_2$ or $NR^I$, wherein $R^I$ is H, $C_{1-6}$-alkyl which may be straight, branched or cyclic, n is 0, 1, 2, 3, 4, 5 and m is 0, 1, 2, 3, 4, 5;
Q is NOH, or O;
Z=O, S, N—$R^{II}$,

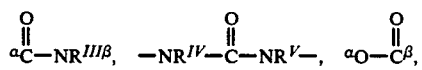

wherein $R^{II}$, $R^{III}$, $R^{IV}$ and $R^V$ independently are hydrogen, benzyl, (C=O)$CF_3$, $C_{1-6}$-acyl, $C_{1-6}$-alkoxy which may be branched or cyclic, or $C_{1-6}$-alkyl which may be straight, branched or cyclic, $CH_2CO_2R^{VI}$ wherein $R^{VI}$ is hydrogen or $C_{1-6}$-alkyl which may be straight or branched;
X is —$(CH_2)_o$— wherein o is 0, 1, 2, or 3;
Y is —$(CH_2)_p$— wherein p is 0, 1, 2 or 3;
α and β indicate attachment points,
and a compound as above having the formula

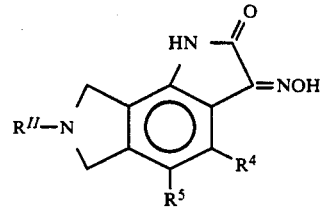

wherein $R^4$, $R^5$ and $R^{II}$ have the meanings set forth above,
and a compound as above having the formula

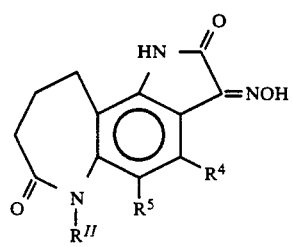

wherein $R^4$, $R^5$ and $R^{II}$ have the meanings set forth above,
and a compound as above having the formula

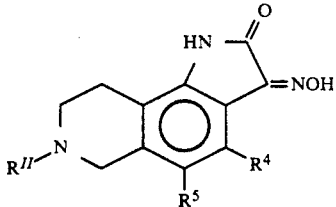

wherein $R^4$ $R^5$ and $R^{II}$ have the meanings set forth above,
and a compound as above having the formula

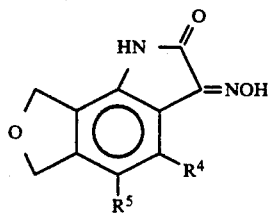

wherein $R^4$ and $R^5$ have the meanings set forth above, and a compound as above having the formula

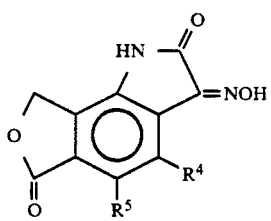

wherein $R^4$ and $R^5$ have the meanings set forth above,
and a method of treating disorders of a mammal, including a human, responsive to the blockade of glutamic and aspartic acid receptors, which comprises administering to a patient in need thereof an effective amount of a compound as first above in unit dosage form,
and a method as above wherein cerebrovascular disorders or psychotic disorders are treated,
and further a pharmaceutical composition comprising a therapeutically-effective amount of a compound as first above together with a pharmaceutically-acceptable carrier,
and a method of preparing a compound having the formula

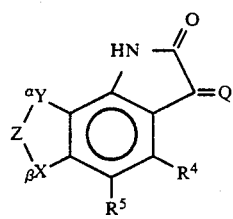

wherein
$R^4$ and $R^5$ independently are hydrogen, halogen, $CF_3$, $CN$, $NO_2$ or $SO_2NR^1R^2$ wherein
$R^1$ is hydrogen or $C_{1-6}$-alkyl which may be straight, branched or cyclic,
$R^2$ is hydrogen or $C_{1-6}$-alkyl which may be straight, branched or cyclic,
or wherein $R^1$ and $R^2$ together represent $-(CH_2)_n-A-(CH_2)_m-$, wherein A is O, S, $CH_2$ or $NR^I$, wherein $R^I$ is H, $C_{1-6}$-alkyl which may be straight, branched or cyclic, n is 0, 1, 2, 3, 4, 5 and m is 0, 1, 2, 3, 4, 5;
Q is NOH, or O;
Z=O, S, N—$R^{II}$,

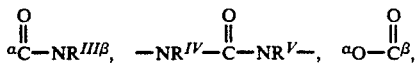

wherein $R^{II}$, $R^{III}$, $R^{IV}$ and $R^V$ independently are hydrogen, benzyl, $(C=O)CF_3$, $C_{1-6}$-acyl, $C_{1-6}$-alkoxy which may be branched or cyclic, or $C_{1-6}$-alkyl which may be straight, branched or cyclic, $CH_2CO_2R^{VI}$ wherein $R^{VI}$ is hydrogen or $C_{1-6}$-alkyl which may be straight or branched;
X is $-(CH_2)_o-$ wherein o is 0, 1, 2, or 3;
Y is $-(CH_2)_p-$ wherein p is 0, 1, 2 or 3;
$\alpha$ and $\beta$ indicate attachment points,
which comprise the step reacting a compound as above wherein Q is oxygen with hydroxylamine or a reactive derivative thereof.

BIOLOGICAL ACTIVITY

The compounds of the invention exhibit valuable biological properties because of their strong excitatory amino acid (EAA) antagonizing properties at the AMPA ((RS)-α-amino-3-hydroxy-5-methyl-4-isoxazolepropionic acid) binding site.

The compound 7-methyl-1,6,7,8-tetrahydrobenzo[2,1-b:3,4-c']dipyrrole-2,3-dione-3-oxime for example exhibit an $IC_{50}$ of 1 μM in the AMPA binding assay as described by T. Honoré et al., Neuroscience Letters 54, 27–32 (1985). In the same assay 1,2,3,6,7,8-hexahydro-3-(hydroxyimino)-N,N,7-trimethyl-2-oxobenzo[2,1-b:3,4-c']dipyrrole-5-sulfonamide has an $IC_{50}$ of 0.3 μM.

The compound 5-nitro-1H,6H-2,3,7,8,9,10-hexahydro-2,3,7-trioxo-azepino[2,3-g]indole-3-oxime in the same test exhibit an $IC_{50}$ of 4 μM.

The compound 7-methyl-1,6,7,8-tetrahydrobenzo[2,1-b:3,4-c']dipyrrole-2,3-dione-3-oxime has an $ED_{50}$ of 8 mg/kg when administered i.v. in the AMPA seizure test as described below.

AMPA-INDUCED CLONIC SEIZURES

AMPA given icv (intracerebroventricular) (15 μg/kg) NMRI to mice induces clonic seizures which should be inhibited by non-NMDA receptor excitatory amino acid antagonists.

Method

Test compound was given i.v. 5 min (or p.o. 30 min) before a 0.3 μg icv administration of AMPA to 10 female NMRI mice (weighing 24–26 g) per dose. The number of mice experiencing clonic seizures within the next 5 min was noted. An $ED_{50}$ value was calculated as the dose inhibiting 50% of the mice from having clonic seizures.

PHARMACEUTICAL COMPOSITIONS

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten milligrams of active ingredients or, more broadly, 0.1 to one hundred (100) milligrams, per tablet, are accordingly suitable representative unit dosage forms.

Solid forms of pharmaceutical compositions for p.o. administration and injectable solutions are preferred.

METHOD OF TREATING

The compounds of this invention are extremely useful in the treatment of central nervous system disorders related to their biological activity. The compounds of this invention may accordingly be administered to a subject, including a human, in need of treatment, alleviation, or elimination of an indication associated with the biological activity of the compounds. This includes especially excitatory amino acid dependent psychosis, excitatory amino acid dependent anoxia, excitatory amino acid dependent ischemia, excitatory amino acid dependent convulsions and excitatory amino acid dependent migraine. Suitable dosage ranges are 0.1 to 1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLE 1 a) 5-nitro-α-tetralone 10 ml (75 mmol) of α-tetralone was added dropwise to 7.6 g (75 mmol) of potassium nitrate dissolved in 75 ml of concentrated sulfuric acid (at −10° C.). The resulting mixture was poured onto ice and the precipitate was suspended in ether. The precipitate (the 7 nitro isomer) was filtered off and the ether solution was evaporated. The residue was purified by column chromatography on silica gel. Yield: 4.7 g of the title compound, M.p. 94°–96° C.

b) 6-nitro-2-oxo-1-benzazepine

The product of example 1a) above, 2.43 g (35 mmol) of hydroxylamine hydrochloride and 3.7 g (35 mmol) of disodium carbonate was added to 100 ml of methanol and the mixture was refluxed for 90 minutes, whereafter it was cooled and neutralized with aqueous acetic acid. The resulting precipitated oxime was isolated (4.3 g), M.p. 139°–141° C. This product was heated with stirring at 110° C. in polyphosphoric acid (50 g) for 30 minutes. The reaction mixture was poured onto crushed ice. This afforded a solid precipitate of the title product which was isolated by filtration and purified by wash with water and ether, M.p. 150°–155° C.

c) 6-amino-2-oxo-1-benzazepine

The product of example 1b) was hydrogenated under standard procedures at 1 atm catalyzed by Pd/C in ethanol. Yield of title compound 2.0 g, M.p. 175°–178° C.

d) 1H,6H-2,3,7,8,9,10-hexahydro-2,3,7-trioxo-azepino[2,3-g]indole

The product of example 1c) and 2 ml (13 mmol) of diethyl ketomalonate in 20 ml of glacial acetic acid was refluxed for four hours, whereafter the mixture was cooled and concentrated by evaporation, the residue was heated (∼60°–80° C.) in 25 ml 5% of NaOH while exposed to air for 2 hours. The mixture was then cooled and concentrated hydrochloric acid was added to pH∼0. The formed precipitate was isolated by filtration. Yield: 0.55 g, M.p. >300° C.

e) 1H,6H-2,3,7,8,9,10-hexahydro-2,3,7-trioxo-azepino[2,3-g]indole-3-oxime 0.23 g of the product of example 1d), 0.1 g (1.3 mmol) of hydroxyl amine hydrochloride and 0.14 g (1.3 mmol) of disodium carbonate was stirred in 10 ml of methanol for 6 hours, whereafter water was added (20 ml). The precipitated product was filtered off. Yield of the title compound 0.2 g, M.p. 256°–258° C.

In a similar manner the following oximes were prepared from the corresponding keto analogs 6,7,9,10-tetrahydro-5-nitro-pyrrolo[2,3-g][2,4]benzodiazepine-2,3,8(1H)trione-3-oxime, M.p. >300° C.

6,7,9,10-tetrahydropyrrolo[2,3-g][2,4]benzodiazepine-2,3,8(1H)trione-3-oxime, M.p. >300° C.

6,8-dihydro-1H-thieno[3,4-g]indole-2,3-dione-3-oxime, M.p. 192°–195° C.

6,8-dihydro-1H-furo[3,4-g]indole-2,3-dione-3-oxime, M.p. >300° C.

8-acetyl-1,6,7,8-tetrahydrobenzo[2,1-b:3,4-b']dipyrrole-2,3-dione-3-oxime, M.p. 244°–245° C.

EXAMPLE 2 a) 5-nitro-1H-6H-2,3,7,8,9,10-hexahydro-2,3,7-trioxoazepino[2,3-g]indole 0.25 g of the product of example 1a) was added to 0.12 g (1.2 mmol) of potassium nitrate in concentrated sulphuric acid (10 ml) at −5° C. after 10 min stirring the reaction mixture was poured onto crushed ice. The resulting mixture was extracted with ethyl acetate, and the organic solvent was allowed to evaporate. This left the title compound as yellow crystals. Yield: 0.1 g, M.p. 277°–278° C.

In the same manner was prepared by nitration 6,7,9,10-tetrahydro-6-nitro-pyrrolo[2,3-g][2,4]benzodiazepine-2,3,8(1H)trione, M.p. >300° C.

b) 5-nitro-1H,6H-2,3,7,8,9,10-hexahydro-2,3,7-trioxoazepino[2,3-g]indole-3-oxime A mixture of the product of example 2a) and 35 mg (0.5 mmol) of hydroxylamine hydrochloride and 53 mg (0.5 mmol) disodium carbonate in 6 ml of methanol was stirred for 2 hours, whereafter water and acetic acid was added to neutral reaction. The precipitate was isolated by filtration. Yield of the title compound 0.1 g, M.p. 232°–234° C.

EXAMPLE 3 a) 2,3-di(bromomethyl)-nitrobenzene 30 g of N-bromo-succinimide (NBS) was added portionwise to 9 g of 2,3-dimethyl-nitrobenzene, and 0.25 ml of t-butyl perbenzoate in 100 ml of carbontetrachloride and the mixture was refluxed for 24 hours. The reaction mixture was thereafter cooled and ether was added. The succinimide was filtered off, and the filtrate was evaporated to give the title compound (18 g) as an oil which could be crystallized from ethanol, M.p. 68°–70° C.

b) N-methyl-4-nitro-2H-1,3-dihydro-pyrrolo[3,4]benzene 20 g of the product of example 3a) was dissolved in 300 ml of methylene chloride at 10° C. Methylamine was led through the solution until TLC shows only small amounts of the starting material left in the solution. The reaction mixture was extracted with water and thereafter with 4N hydrochloric acid (150 ml). pH of the aqueous phase was adjusted to 10 with 4N NaOH. This treatment left the title compound as pale crystals which was isolated by filtration. Yield of the title compound as the hydrochloride 2.5 g, M.p. >300° C.

In a similar manner the following compounds were prepared

N-t-butyl-4-nitro-2H-1,3-dihydro-pyrrolo[3,4]benzene, M.p. 233°-235° C. (hydrochloride) from reaction with t-butyl amine.

N-ethyl-4-nitro-2H-1,3-dihydro-pyrrolo[3,4]benzene, M.p. 250° C. (decomposes) from reaction with ethylamine.

N-benzyl-4-nitro-2H-1,3-dihydro-pyrrolo[3,4]benzene, M.p. 238°-239° C. (hydrochloride) from reaction with benzylamine.

N-methoxy-4-nitro-2H-1,3-dihydro-pyrrolo[3,4]benzene hydrochloride from reaction with O-methylhydroxyl-amine hydrochloride oil.

c) 1,2,4,5-tetrahydro-5-nitro-3-oxo[2,4]benzodiazepine 2,3-di-aminomethyl-nitrobenzene, M.p. 93°-95° C.

A mixture of potassium phthalimid (11 mmol) and 2,3-dibromomethyl-nitrobenzene (5 mmol) was stirred at reflux temperature in THF (30 ml) and DMF (10 ml) for 2 hours.

The formed precipitate was filtered off and treated with hydrazine hydrate (0.75 ml) in methanol (50 ml). This mixture was refluxed for 3 hours, cooled to room temperature and filtered. The filtrate was evaporated, and the residue was stirred in $CH_2Cl_2$. The filtrated $CH_2Cl_2$ solution was then evaporated to give the title compound as light pink crystals, M.p. 93°-95° C.

10 mmol of the product described above was dissolved in dry DMF (50 ml). N,N-carbonyldiimidazole (15 mmol) was added, whereafter the solution was refluxed for 2 hours. After cooling, the precipitated product was filtered off as white crystals, M.p. 260°-265° C. (decomp.).

d) 2-methyl-4-amino-2H-1,3-dihydro-pyrrolo[3,4]benzene hydrochloride 4.2 g of the product of example 3b was hydrogenated under standard procedure with Pd/C as catalyst in ethanol. Yield: 3.2 g of the title compound, M.p. 147°-150° C.

The following amines were likewise obtained by hydrogenation from the corresponding nitro analogs.

2-t-butyl-4-amino-2H-1,3-dihydro-pyrrolo[3,4]benzene hydrochloride oil.

2-benzyl-4-amino-2H-1,3-dihydro-pyrrolo[3,4]benzene hydrochloride oil.

2-methoxy-4-amino-2H-1,3-dihydro-pyrrolo[3,4]benzene hydrochloride oil.

1-acetyl-7-amino indoline, M.p. 156°-158° C. from hydrogenation of 1-acetyl-5-bromo-7-nitro indoline.

3-amino-benzo[3,4]butyro lactone hydrochloride, M.p. 227°-230° C.

4-amino-1,3-dihydro benzo[c]furan hydrochloride, M.p. 238°-241° C.

1,2,4,5-tetrahydro-5-amino-3-oxo-2,4-benzodiazepine, M.p. 222°-224° C.

4-amino-1,3-dihydro benzo[c]thiophene oil. Raney Ni was used as catalysist.

5-amino-2-methyl-1,2,3,4-tetrahydro isoquinoline. Oil from hydrogenation of 2-methyl-5-nitro isoquinolinium methyl sulphate with $PtO_2$ at catalysist.

e) 7-methyl-1,6,7,8-tetrahydrobenzo[2,1-b:3,4-c']dipyrrole-2,3-dione 2.2 g of the product of example 3d), 3.0 g of hydroxylamine hydrochloride, 1.93 ml of chlorale in 70 ml water and 16 g of disodium sulphate was heated to 100° C. for 30 min. The solution was cooled and pH adjusted to 8 with $Na_2CO_3$. This afforded a crystalline precipitate which was filtered off and washed with water. After drying, the crystals were dissolved in 20 ml of concentrated sulphuric acid and heated with stirring to 100° C. for 15-20 minutes. The mixture was cooled and crushed ice 100 g was added followed by 15 ml of 30% sodium hydroxide. Thereafter saturated aqueous disodium carbonate was added until pH was 9. The formed precipitate was isolated, and was thereafter recrystallized from ethanol. Yield of the title compound 1.6 g, M.p. 163°-165° C.

In a similar manner were prepared 7-(1,1-dimethylethyl)-1,6,7,8-tetrahydrobenzo[2,1-b:3,4-c']dipyrrole-2,3-dione, M.p. 178°-180° C.

7-ethyl-1,6,7,8-tetrahydrobenzo[2,1-b:3,4-c']dipyrrole-2,3-dione, M.p. 168°-170° C.

1,6,7,8-tetrahydro-7-methoxybenzo[2,1-b:3,4-c']dipyrrole-2,3-dione, M.p. 174°-176° C.

1,6,7,8-tetrahydro-7-(phenylmethyl)benzo[2,1-b::3,4-c']dipyrrole-2,3-dione, M.p. >300° C.

6,8-dihydro-1H-thieno[3,4-g]indole-2,3-dione, M.p. >300° C.

6,8-dihydro-1H-furo[3,4-g]indole-2,3-dione, M.p. >300° C.

8-acetyl-1,6,7,8-tetrahydrobenzo[2,1-b:3,4-b']dipyrrole-2,3-dione, M.p. >300° C.

6,7,9,10-tetrahydropyrrolo[2,3-g][2,4]benzodiazepine-2,3,8(1H)-trione, M.p. >300° C.

1H-furo[3,4-g]indole-2,3,6(8H)-trione, M.p. >300° C.

6,7,8,9-tetrahydro-7-methyl-1H-pyrrolo[2,3-f]isoquinoline-2,3-dione, M.p. >300° C.

6,7,8,9-tetrahydro-7-ethoxycarbonylmethyl-1H-pyrrolo[2,3-f]isoquinoline-2,3-dione, M.p. 180°-183° C.

6,7,8,9-tetrahydro-7-trifluoroacetyl-1H-pyrrolo[2,3-f]isoquinoline-2,3-dione, M.p. 216°-219° C.

6,7,8,9-tetrahydro-7-acetyl-1H-pyrrolo[2,3-f]isoquinoline-2,3-dione, M.p. 248°-250° C.

EXAMPLE 4

7-acetyl-6,7,8,9-tetrahydro-5-nitro-1H-pyrrolo[2,3-f]isoquinoline-2,3-dione, M.p. >300° C. was obtained from nitration of 7-acetyl-6,7,8,9-tetrahydro-1H-pyrrolo[2,3-f]isoquinoline-2,3-dione in 98% sulphuric acid and $KNO_3$.

EXAMPLE 5

5-bromo-1,6,7,8-tetrahydro-7-methylbenzo[2,1-b:3,4-c']dipyrrole-2,3-dione

To a stirred suspension of 1,6,7,8-tetrahydro-7-methylbenzo[2,1-b:3,4-c']dipyrrole-2,3-dione (0.5 g, 2.48 mmol) in water (20 ml) was added a solution of bromine (0.7 ml) in ethanol (5 ml). After 5 hours stirring at room temperature the reaction was completed and pH was adjusted to 8 with sat $Na_2CO_3$. The precipitated product was filtered off and washed with water, M.p. >300° C.

Substitution of bromine with chlorine gave likewise 5-chloro-1,6,7,8-tetrahydro-7-methylbenzo[2,1-b:3,4-c']dipyrrolo-2,3-dione, M.p. >300° C.

EXAMPLE 6

6,7,8,9-tetrahydro-1H-pyrrolo[2,3-f]isoquinoline-2,3-dione

To an ice cooled stirred suspension of 6,7,8,9-tetrahydro-7-methyl-1H-pyrrolo[2,3-f]isoquinoline-2,3-dione (500 mg) in 1,2-dichloroethane (10 ml) was added α-chloroethylchloroformate (0.25 ml). The mixture was then brought to reflux for 1 hour, whereafter it was cooled to room temperature and filtered. The filtrate was evaporated, the residue dissolved in methanol (10 ml) and refluxed for 10 min. Evaporation of the solvent left the crude title compound as a solid, M.p. 270° C.

EXAMPLE 7

7-(1,1-dimethylethyl)-1,2,3,6,7,8-hexahydro-3-(hydroxyimino)-N,N-dimethyl-2-oxobenzo[2,1-b:3,4-c']dipyrrole-5-sulphonamide 1,6,7,8-tetrahydro-7-(dimethylethyl)benzo[2,1-b:3,4-c']dipyrrole-2,3-dione (0.5 g) was dissolved in chlorosulphonic acid (2 ml). The solution was heated to 80° C. for 10-20 min, then cooled and the excess of chlorosulphonic acid was destroyed by addition of neat NaCl, followed by addition of 2 ml water. After some time a precipitate of 7-(dimethylethyl)-1,2,3,6,7,8-hexahydro-3,3-dichloro-2-oxobenzo[2,1-b:3,4-c']dipyrrole-5-sulphonylchloride, hydrochloride was formed. The precipitate was filtered off, washed with 4N HCl and dried. Thereafter it was brought into solution in dry THF (20 ml), undissolved inorganic material was removed by filtration. To the THF solution was added dimethylamine until complete reaction (followed by TLC). The reaction mixture was filtered and the solvent was removed by evaporation. This left the crude 7-(1,1-dimethylethyl)-1,2,3,6,7,8-hexahydro-3,3-dichloro-N,N-dimethyl-2-oxobenzo[2,1-b:3,4-c']dipyrrole-5-sulphonamide as a oily residue which was reacted with hydroxylamine, hydrochloride (100 mg) in refluxing methanol (5 ml).

After 1 hour reflux the reaction mixture was cooled to ambient temperature and the product (title compound) was filtered off as the monohydrochloride, M.p. (free base) 242°-244° C.

In a similar manner was prepared 7-ethyl-1,2,3,6,7,8-hexahydro-3-(hydroxyimino)-N,N-dimethyl-2-oxobenzo[2,1-b:3,4-c']dipyrrole-5-sulphonamide monohydrochloride, M.p. >300° C.

1,2,3,6,7,8-hexahydro-3-(hydroxyimino)-N,N,7-trimethyl-2-oxobenzo[2,1-b:3,4-c']dipyrrole-5-sulfonamide, M.p. >300° C.

1,2,3,6,7,8-hexahydro-3-(hydroxyimino)-N,N,7-trimethyl-2-oxobenzo[2,1-b:3,4-c']dipyrrole-5-sulfonamide monohydrochloride, M.p. >300° C.

1,2,3,6,7,8-hexahydro-3-(hydroxyimino)-N,7-dimethyl-2-oxobenzo[2,1-b:3,4-c']dipyrrole-5-sulfonamide monohydrochloride, M.p. >300° C.

1-[[1,2,3,6,7,8-hexahydro-3-(hydroxyimino)-7-methyl-2-oxobenzo[2,1-b:3,4-c']dipyrrole-5-yl]sulfonyl]pyrrolidine monohydrochloride, M.p. >300° C.

1,2,3,6,7,8-hexahydro-3-(hydroxyimino)-7-methyl-2-oxobenzo[2,1-b:3,4-c']dipyrrole-5-sulfonamide monohydrochloride, M.p. >300° C.

2,3,6,7,8,9-hexahydro-3-(hydroxyimino)-N,N,7-trimethyl-2-oxo-1H-pyrrolo[2,3-f]isoquinoline-5-sulfonamide monohydrochloride., M.p. 268° C.

7-acetyl-5-(N,N-dimethylsulphamoyl)-6,7,8,9-tetrahydro-1H-pyrrolo[2,3-f]isoquinoline-2,3-dione-3-oxime, M.p. 260°-261° C.

EXAMPLE 8

7-methyl-1,6,7,8-tetrahydrobenzo[2,1-b:3,4-c']dipyrrole-2,3-dione-3-oxime 200 mg of the product of example 3e), 150 mg of disodium carbonate and 100 mg of hydroxylamine hydrochloride in 20 ml methanol was stirred for 3 hours at reflux temperature. Then water and acetic acid was added to the reaction mixture and sodium hydrogen carbonate was thereafter added until pH~8. The crystalline precipitate was isolated by filtration. Yield of the title compound 200 mg, M.p. >300° C.

In a similar manner were prepared 7-(1,1-dimethylethyl)-1,6,7,8-tetrahydrobenzo[2,1-b:3,4-c']dipyrrole-2,3-dione-3-oxime, M.p. 242°-244° C.

7-ethyl-1,6,7,8-tetrahydrobenzo[2,1-b:3,4-c']dipyrrole-2,3-dione-3-oxime, hydrochloride, M.p. >300° C.

1,6,7,8-tetrahydro-7-methoxybenzo[2,1-b:3,4c']-dipyrrole-2,3-dione-3-oxime, M.p. >300° C.

1,6,7,8-tetrahydro-7-(phenylmethyl)benzo[2,1-b:3,4-c']-dipyrrole-2,3-dione-3-oxime, M.p. >300° C.

6,7,8,9-tetrahydro-7-methyl-1H-pyrrolo[2,3-f]isoquinoline-2,3-dione-3-oxime, M.p. 193°-195° C.

6,7,8,9-tetrahydro-1H-pyrrolo[2,3-f]isoquinoline-2,3-dione-3-oxime, hydrochloride, M.p. >300° C.

7-acetyl-6,7,8,9-tetrahydro-1H-pyrrolo[2,3-f]isoquinoline-2,3-dione-3-oxime, M.p. 190°-193° C.

7-acetyl-5-nitro-6,7,8,9-tetrahydro-1H-pyrrolo[2,3-f]isoquinoline-2,3-dione-3-oxime, M.p. 217°-219° C.

6,7,8,9-tetrahydro-7-trifluoroacetyl-1H-pyrrolo[2,3-f]isoquinoline-2,3-dione-3-oxime, M.p. 251°-253° C.

7-ethoxycarbonylmethyl-6,7,8,9-tetrahydro-1H-pyrrolo-[2,3-f]isoquinoline-2,3-dione-3-oxime, M.p. 212°-214° C.

We claim:

1. A compound having the formula

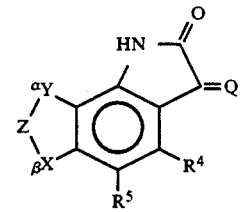

wherein $R^4$ and $R^5$ independently are hydrogen, halogen, $CF_3$, CN, $NO_2$ or $SO_2NR^1R^2$ wherein $R^1$ is hydrogen or $C_{1-6}$-alkyl which may be straight, branched or cyclic, $R^2$ is hydrogen or $C_{1-6}$-alkyl which may be straight, branched or cyclic, or wherein $R^1$ and $R^2$ together represent —(CH$_2$)$_n$—A—(CH$_2$)$_m$—, wherein A is O, S, CH$_2$ or NR$^J$, wherein R$^J$ is H, $C_{1-6}$-alkyl which may be straight, branched or cyclic, n is 0, 1, 2, 3, 4, 5 and m is 0, 1, 2, 3, 4, 5;

Q is NOH or O;

Z=O, S, N—R$^{II}$, $$\overset{\alpha}{C}-NR^{III}\beta, \quad -NR^{IV}-\overset{O}{\underset{\|}{C}}-NR^{V}-, \quad \overset{\alpha}{O}-\overset{O}{\underset{\|}{C}}\beta,$$

wherein $R^{II}$, $R^{III}$, $R^{IV}$ and $R^V$ independently are hydrogen, benzyl, (C=O)CF$_3$, C$_{1-6}$carboxylic acid-acyl, C$_{1-6}$-alkoxy which may be branched or cyclic, or C$_{1-6}$-alkyl which may be straight, branched or cyclic, CH$_2$CO$_2$R$^{VI}$ wherein R$_{VI}$ is hydrogen or C$_{1-6}$-alkyl which may be straight or branched;

X is —(CH$_2$)$_o$— wherein o is 0, 1, 2, or 3;
Y is —(CH$_2$)$_p$— wherein p is 0, 1, 2 or 3;
α and β indicate attachment points.

2. A compound of claim 1 having the formula

[structure]

wherein R$^4$, R$^5$ and R$^{II}$ have the meanings set forth above.

3. A compound of claim 1 having the formula

[structure]

wherein R$^4$, R$^5$ and R$^{II}$ have the meanings set forth above.

4. A compound of claim 1 having the formula

[structure]

wherein R$^4$, R$^5$ and R$^{II}$ have the meanings set forth above.

5. A compound of claim 1 having the formula

[structure]

wherein R$^4$ and R$^5$ have the meanings set forth above.

6. A compound of claim 1 having the formula

[structure]

wherein R$^4$ and R$^5$ have the meanings set forth above.

7. A pharmaceutical composition useful for treatment of a disorder of a mammal which is responsive to the blockage of glutamic and aspartic acid receptors, comprising an amount of a compound of claims 1 which is effective for such purpose together with a pharmaceutically-acceptable carrier.

8. A method of treating a disorder of a mammal, including a human, responsive to the blockade of glutamic and aspartic acid receptors, which comprises administering to a patient in need thereof an effective amount of a compound of claim 1 in unit dosage form.

9. The method of claim 8 wherein cerebrovascular disorders or psychotic disorders are treated.

10. A method of preparing a compound having the formula

[structure]

wherein
R$^4$ and R$^5$ independently are hydrogen, halogen, CF$_3$, CN, NO$_2$ or SO$_2$NR$^1$R$^2$ wherein
R$^1$ is hydrogen or straight, C$_{1-6}$-alkyl which may be branched or cyclic,
R$^2$ is hydrogen or straight, C$_{1-6}$-alkyl which may be branched or cyclic,
or wherein R$^1$ and R$^2$ together represent —(CH$_2$)$_n$—A—(CH$_2$)$_m$—,
wherein A is O, S, CH$_2$ or NR$^J$, wherein R$^J$ is H, C$_{1-6}$-alkyl which may be straight, branched or cyclic, n is 1, 2, 3, 4, 5 and m is 0, 1, 2, 3, 4, 5;
Q is NOH, O;
Z = O, S, N—R$^{II}$, $$\overset{\alpha}{C}-NR^{III}\beta, \quad -NR^{IV}-\overset{O}{\underset{\|}{C}}-NR^{V}-, \quad \overset{\alpha}{O}-\overset{O}{\underset{\|}{C}}\beta,$$

wherein $R^{II}$, $R^{III}$, $R^{IV}$ and $R^V$ independently are hydrogen, benzyl, (C=O)CF$_3$, C$_{1-6}$carboxylic acid-acyl, C$_{1-6}$-alkoxy which may be branched or cyclic, or C$_{1-6}$-alkyl which may be straight, branched or cyclic, CH$_2$CO$_2$R$^{VI}$ wherein R$^{VI}$ is hydrogen or C$_{1-6}$-alkyl which may be straight or branched;

X is —(CH$_2$)$_o$— wherein o is 0, 1, 2, or 3;
Y is —(CH$_2$)$_p$— wherein p is 0, 1, 2 or 3;
α and β indicate attachment points,
which comprises the step of reacting a compound having the formula given above, wherein Q is O, with hydroxylamine or a reactive derivative thereof.

* * * * *

UNITED STATES PATENT AND TRADEMARK OFFICE
CERTIFICATE OF CORRECTION

PATENT NO. : 5,242,918

DATED : September 7, 1993

INVENTOR(S) : Frank Wätjen, Bjarne H. Dahl, Jørgen Drejer and Leif H. Jensen

It is certified that error appears in the above-indentified patent and that said Letters Patent is hereby corrected as shown below:

Title Page, [54], first line of the title; "ISATINOXIME" should be -- ISATINEOXIME --

Title Page, [57], ABSTRACT, line 9 from bottom; "$C_{1-6}$carboxylic acid-acyl," should read -- $C_{1-6}$-carboxylic acid acyl, --

Col. 1, line 1; "ISATINOXIME" should be -- ISATINEOXIME --

Col. 2, line 24; delete the comma "," after "NOH"
Col. 3, approximately line 11; insert a comma -- , -- after -- $R^4$ --
Col. 4, line 6; delete ", or O"
Col. 5, line 10; insert -- (10) -- after "ten"
Col. 8, line 2; "catalysist" should read -- catalyst --
Col. 8, lines 5 & 6; "Pto$_2$ at catalysist" should read -- PtO$_2$ as catalyst --
Col. 8, line 32; "-b::3,4-" should read -- -b:3,4- --
Col. 10, line 25; "4c']" should read -- 4-c'] --
Col. 10, line 35; "[2,3" should read -- [2,3-f]- --
Col. 10, line 36; delete "-f]"
Col. 11, lines 6 & 7; "$C_{1-6}$carboxylic acid-acyl," should read -- $C_{1-6}$-carboxylic acid acyl, --
Col. 12, line 48; "is 1," should read -- is 0, 1, --
Col. 12, line 49; "NOH, O;" should read -- NOH; --

UNITED STATES PATENT AND TRADEMARK OFFICE
CERTIFICATE OF CORRECTION

PATENT NO. : 5,242,918
DATED : September 7, 1993
INVENTOR(S) : Frank Wätjen, Bjarne H. Dahl, Jørgen Drejer and Leif H. Jensen It is certified that error appears in the above-indentified patent and that said Letters Patent is hereby corrected as shown below:

Col. 12, lines 56 & 57; "$C_{1-6}$carboxylic acid-acyl," should read --$C_{1-6}$-carboxylic acid acyl,--.

Signed and Sealed this

Twenty-eighth Day of June, 1994

*Attest:*

BRUCE LEHMAN

*Attesting Officer*  *Commissioner of Patents and Trademarks*